(12) United States Patent
Kang et al.

(10) Patent No.: US 12,318,215 B2
(45) Date of Patent: Jun. 3, 2025

(54) STIMULUS PROVIDING DEVICE, PERCEPTION TRAINING METHOD, AND COMPUTER PROGRAM

(71) Applicant: NUNAPS INC., Seoul (KR)

(72) Inventors: Dong Wha Kang, Seoul (KR); Rak Kyeun Hong, Guri-si (KR)

(73) Assignee: NUNAPS INC., Seoul (KR)

( * ) Notice: Subject to any disclaimer, the term of this patent is extended or adjusted under 35 U.S.C. 154(b) by 790 days.

(21) Appl. No.: 17/321,619

(22) Filed: May 17, 2021

(65) Prior Publication Data

US 2021/0267538 A1    Sep. 2, 2021

Related U.S. Application Data

(63) Continuation of application No. PCT/KR2020/000459, filed on Jan. 10, 2020.

(30) Foreign Application Priority Data

Jan. 11, 2019  (KR) .................. 10-2019-0004023
Jan. 10, 2020  (KR) .................. 10-2020-0003472

(51) Int. Cl.
*A61B 5/00*  (2006.01)
*A61B 5/377*  (2021.01)
(Continued)

(52) U.S. Cl.
CPC .............. *A61B 5/483* (2013.01); *A61B 5/377* (2021.01); *A61B 5/383* (2021.01); *A61B 5/6802* (2013.01); *G16H 10/20* (2018.01); *A61B 2560/04* (2013.01)

(58) Field of Classification Search
CPC ..... A61B 5/4824; A61B 5/4827; G16H 10/20
See application file for complete search history.

(56) References Cited

U.S. PATENT DOCUMENTS

2005/0075593 A1* 4/2005 Smith ............... A61F 5/028
                                                                    602/2
2006/0129060 A1* 6/2006 Lee .................. A61B 5/0537
                                                                    600/547
(Continued)

FOREIGN PATENT DOCUMENTS

JP    2016-511651 A    4/2016
JP    2017-023781 A    2/2017
(Continued)

*Primary Examiner* — Daniel L Cerioni
(74) *Attorney, Agent, or Firm* — Studebaker Brackett PLLC (57) ABSTRACT

The inventive concept relates to a stimulus providing device that provides training stimuli for improving pain of a pain patient, a perception training method, and a computer program. The stimulus providing device for providing a training stimulus for improving pain includes one or more mounting units mounted on body portions of a user, and one or more stimulus providing units disposed in the mounting units and which provides stimuli to the body portions, the stimulus providing units are controlled by a control unit included in the stimulus providing device or a control unit physically separated from the stimulus providing device to interwork with the stimulus providing device and included in a terminal of the user, and the control unit controls at least one of a location, a range, and an intensity of the stimuli.

8 Claims, 9 Drawing Sheets

(51) Int. Cl.
*A61B 5/383* (2021.01)
*G16H 10/20* (2018.01)

(56) References Cited

U.S. PATENT DOCUMENTS

| | | | | |
|---|---|---|---|---|
| 2010/0107657 | A1* | 5/2010 | Vistakula | A41D 13/0056 62/3.5 |
| 2011/0245708 | A1* | 10/2011 | Finkel | A61N 1/36071 600/544 |
| 2015/0148865 | A1* | 5/2015 | Gozani | A61N 1/36014 607/46 |
| 2017/0014625 | A1* | 1/2017 | Rosenbluth | A61B 5/1101 |
| 2018/0000685 | A1* | 1/2018 | Maloney | A61N 1/36031 |
| 2019/0091471 | A1* | 3/2019 | Timms | A61N 1/36021 |

FOREIGN PATENT DOCUMENTS

| | | |
|---|---|---|
| JP | 2017-140448 A | 8/2017 |
| KR | 10-0550666 B1 | 2/2006 |
| KR | 10-2010-0085466 A | 7/2010 |
| KR | 10-1592089 A | 2/2016 |
| WO | 2017/187202 A1 | 11/2017 |

* cited by examiner

STIMULUS PROVIDING DEVICE, PERCEPTION TRAINING METHOD, AND COMPUTER PROGRAM

CROSS-REFERENCE TO RELATED APPLICATIONS

The present application is a continuation of International Patent Application No. PCT/KR2020/000459, filed on Jan. 10, 2020, which is based upon and claims the benefit of priority to Korean Patent Application Nos. 10-2019-0004023 filed on Jan. 11, 2019 and 10-2020-0003472 filed on Jan. 10, 2020. The disclosures of the above-listed applications are hereby incorporated by reference herein in their entirety.

BACKGROUND

Embodiments of the inventive concept described herein relate to a stimulus providing device, a perception training method, and a computer program, and more particularly, to a stimulus providing device that provides training stimuli for improving pain of a pain patient, a perception training method, and a computer program.

Conventionally, various perception training methods for recognizing stimuli rightly by patients having a nerve disorder symptoms due to innate and acquired causes have been provided.

Meanwhile, the conventional perception training method has been developed to activate sensory organs suffering from deterioration of functions in a simple approach method.

However, the nerve routes of a human being are not simple, and for example, in relation to chronic pain, in addition to a negative symptom (hardness of hearing), chronic pain due to a positive symptom (a secondary disorder of feeling senses in another method after the functions deteriorate, ringing) is caused.

Accordingly, a perception training method for improving perception abilities by training the brain of a patient in various stimulation methods is necessary.

SUMMARY

Embodiments of the inventive concept provide a stimulus providing device that may train a patient having a nerve disorder symptom in various stimulation methods, a perception training method using the stimulus providing device, and a computer program stored in a medium to execute the perception training method.

The technical objects of the inventive concept are not limited to the above-mentioned ones, and the other unmentioned technical objects will become apparent to those skilled in the art from the following description.

According to an embodiment, a stimulus providing device for providing a training stimulus for improving pain includes one or more mounting units mounted on body portions of a user, and one or more stimulus providing units disposed in the mounting units and which provides stimuli to the body portions, the stimulus providing units are controlled by a control unit included in the stimulus providing device or a control unit physically separated from the stimulus providing device to interwork with the stimulus providing device and included in a terminal of the user, and the control unit controls at least one of a location, a range, and an intensity of the stimuli.

The control unit may detect a timing, at which a sensory stimulus is not input to the user, and manually output stimuli through the stimulus providing units at the detected timing.

The control unit may, while adjusting the intensities of the stimuli by stages, receive whether pain is felt due to the intensities of the stimuli adjusted by stages and determine appropriate intensities of stimuli.

The control unit may interwork with a brainwave measuring device, which is physically separated from the stimulus providing device, to determine the appropriate intensities of stimuli, brain activation levels of which are maintained at a reference value or more while the user does not feel pain.

The control unit may control the one or more stimulus providing units to sequentially provide the stimuli to a specific body portion of the user or simultaneously provide the stimuli to a plurality of body portions of the user, distinguish a stimulus provided to the user, request the user to select an answer corresponding to the distinguished stimuli, and determine the selected answer is a correct answer, and the correct answer may be a stimulus that coincides with a specific condition or different stimuli among three or more stimuli.

The stimulus providing units may include one or more first strips that provides a first temperature that is higher than a temperature of a body surface of the user to the body portions of the user, and one or more second strips that provides a second temperature that is lower than the temperature of the body surface of the user to the body portions of the user, the first strips and the second strips may be arranged in a form of a stripe pattern, in which the first strips and the second strips are alternately arranged, the stimulus providing units may include a plurality of heat emitters, and the control unit may control the stimulus providing units in a heat retaining mode and a stimulus providing mode.

The mounting units may include a first mounting unit mounted on a normal body portion of the user, and a second mounting unit mounted on an abnormal body portion of the user, and the stimulus providing units may include a first stimulus providing unit disposed in the first mounting unit and which provides a stimulus to the normal body portion, and a second stimulus providing unit disposed in the second mounting unit and which provides a stimulus to the abnormal body portion.

According to another embodiment, a perception training method using a stimulus providing device for providing a training stimulus for improving pain includes sequentially providing a plurality of stimuli generated by the stimulus providing device mounted on body portions of a user to a specific body portion of the user or simultaneously providing the plurality of stimuli to a plurality of body portions of the user, wherein at least one of a location, a range, and an intensity of the plurality of stimuli is different, distinguishing a stimulus provided to the user, requesting the user to select an answer corresponding to the distinguished stimulus, and determining whether the selected answer of the user is a correct answer.

According to an embodiment, a computer program stored in a recording medium to execute a perception training method using a stimulus providing device coupled to a computer that is hardware to provide a training stimulus for improving pain, wherein the computer program executes operations of sequentially providing a plurality of stimuli generated by the stimulus providing device mounted on body portions of a user to a specific body portion of the user or simultaneously providing the plurality of stimuli to a plurality of body portions of the user, wherein at least one of a location, a range, and an intensity of the plurality of stimuli is different, distinguishing a stimulus provided to the user, requesting the user to select an answer corresponding to the distinguished stimulus, and determining whether the selected answer of the user is a correct answer.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art, to which the inventive concept pertains, and the inventive concept will be defined by the scope of the claims.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals denote the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms, such as "below", "beneath", "lower", "above", and "upper", which are spatially relative may be used to easily describe a correlation between one element and other elements as illustrated in the drawings. The spatially relative terms have to be understood as terms including different directions of the elements during use or an operation, in addition to the direction illustrated in the drawings. For example, when the elements illustrated in the drawings are overturned, the elements "below" or "beneath" another element may be positioned "above" the other element. Accordingly, the term "below" or "beneath" may include "below" or "beneath" and "above". The element may be oriented in different directions, and accordingly, the spatially relative terms may be construed according to the orientation.

Hereinafter, a stimulus providing device 10 of the inventive concept will be described with reference to the drawings. FIGS. 1A to 1D and 2 are conceptual views illustrating various embodiments of a mounting unit of a stimulus providing device of the inventive concept. FIGS. 3A to 3C are conceptual views illustrating various embodiments of a stimulus providing unit of a stimulus providing device of the inventive concept.

The stimulus providing device 10 according to embodiments of the inventive concept may be provided in a form of a wearable device (for example, a mounted or attached wearable device), and may provide stimuli to a user in various schemes to perform perception training. The schemes of providing stimuli by various wearable devices will be described in detail later.

Meanwhile, the stimulus providing device 10 according to the embodiments of the inventive concept may be applied to patients who suffer from various diseases. As an example, the stimulus providing device 10 of the inventive concept may be applied to a perception disorder patient. In particular, it may be applied to a chronic pain patient, and in this case, the chronic pain may be a neuropathic disease or an inflammatory disease. Furthermore, the stimulus providing device 10 may be also applied to a treatment of a hand shaking patient due to a disorder of a nervous system. A detailed description of a scheme of treating the diseases by using the stimulus providing device for each disease will be made later.

The stimulus providing device 10 according to the embodiments of the inventive concept may provide training in conjunction with various devices.

As an embodiment, the stimulus providing device 10 may be paired with a user terminal (not illustrated) while being used. In this case, the user terminal may include one or more of electric communication devices, such as smartphone, a tablet, a PDA, a laptop computer, and a remote controller, but the inventive concept is not limited thereto.

In this case, the stimulus providing device 10 of the inventive concept may be controlled (for example, setting of a difficulty level of a training) by the user terminal, a training result may be stored in a database and may be managed by the user terminal (for example, daily training records), and conditions of the user may be monitored in real time by the user terminal and be provided to a guardian.

Furthermore, the user terminal or an application that is operated in conjunction with the stimulus providing device 10 may be connected to a central management server of a hospital to share a training result with a medical expert, and through this, the medical expert may monitor whether the user performed training and the like.

Furthermore, in another embodiment, the stimulus providing device 10 may be connected to a virtual reality (VR) and augmented reality (AR) device to be used. The stimulus providing device 10 may interwork with a virtual reality space implementing device (for example, a head mounted display device) to be used, and may be manufactured of some elements of the virtual reality and augmented reality device. For example, the stimulus providing device 10 may be embedded in a glove for VR that detects a motion of a hand of the user. The stimulus providing device 10 may provide various trainings as it is operated in conjunction with the virtual reality (VR) or augmented reality (AR) display device, and a detailed description thereof will be made later. As an example, when the stimulus providing device 10 of the inventive concept provides a skin stimulus (for example, provides a temperature stimulus in an actual reality), the virtual reality and augmented reality device may provide various visual contents (for example, provide an image displaying that a thermal conductor contacts a body portion, to which a skin stimulus is applied, in a virtual and augmented reality) to help the user perceive the skin stimulus in the actual reality.

In detail, the stimulus providing device 10 may provide a stimulus for treating pain to a body portion, on which the stimulus providing device is mounted, while providing visual contents as it is operated in conjunction with an HMD for VR. That is, a haptic perception learning effect for improving pain may be improved by forming a temporal-spatial relationship between a visual stimulus and a haptic stimulus.

The stimulus providing device 10 may provide a stimulus corresponding to visual contents, by which a visual percept and a haptic perception may be associated with each other through a virtual reality HMD while providing the visual contents.

For example, in order to provide a stimulus, in which a visual perception and a haptic perception are mixed, for increasing the reality and the immersion, the stimulus providing device 10 may provide a temperature stimulus to help the user feel warm while providing visual contents, in which the user approaches a warm object, through the HMD. The stimulus providing device 10 may lead the sensory system to be normalized while providing a stimulus generated in the actual reality to a virtual space.

Furthermore, for example, a feedback that has to be output from contents watched by a patient may be generated by a stimulus output by the stimulus providing device 10. Through a multimodal stimuli that are related to each other temporally and spatially, an effect of haptic perception learning may be improved.

The stimulus providing device 10 of the inventive concept may include one or more mounting units 11 and one or more stimulus providing units 12. The mounting units 11 may be provided in a wearable form and be mounted on body portions of the user. The body portions, to which the stimulus providing device 10 of the inventive concept provides stimuli, may be determined by the mounting units 11.

Figure 1A:
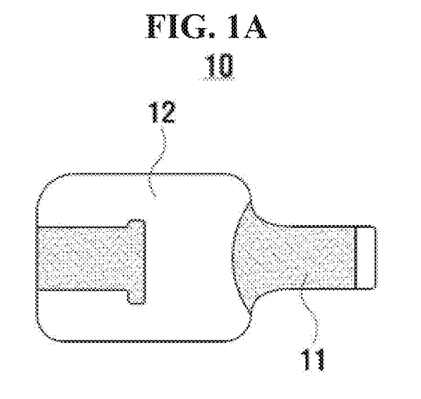
FIGS. 1A to 1D and 2 are conceptual views illustrating various embodiments of a mounting unit of a stimulus providing device of the inventive concept.
Figure 1B:
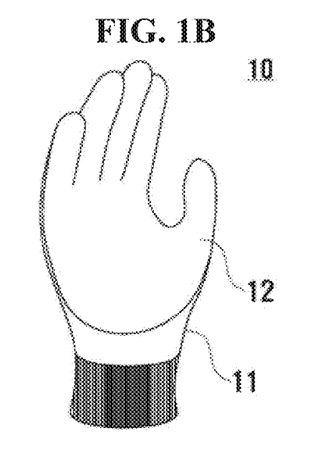
Figure 1C:
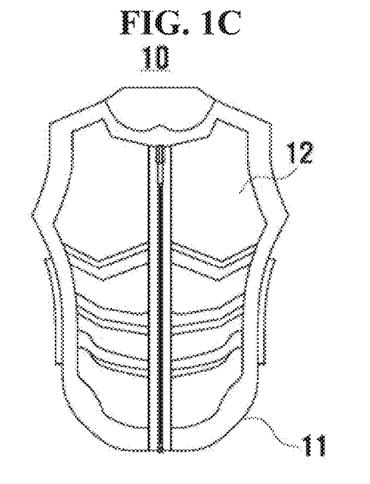
Figure 1D:
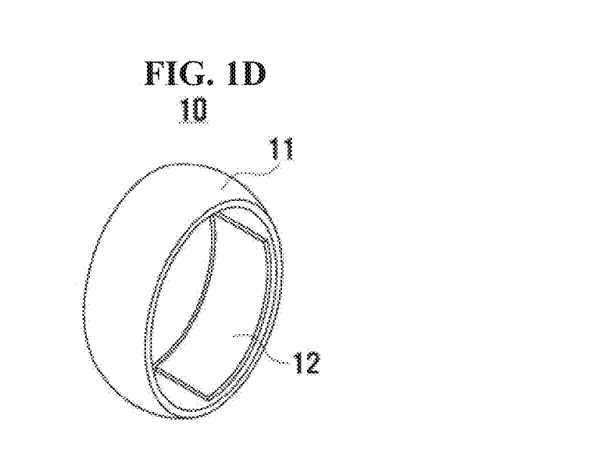

As illustrated in FIGS. 1A to 1D, the mounting units 11 may be implemented in various embodiments. As an example, the mounting units 11 may be provided in a wearable band form as illustrated in FIG. 1A, may be provided in a glove form as illustrated in FIG. 1B, may be provided in a suit form as illustrated in FIG. 1C, and may be provided in a ring or torso form as illustrated in FIG. 1D.

The stimulus providing units 12 may be disposed in the mounting units 11, or may provide stimuli to the body portions.

The stimulus providing units 12 may provide various kinds of stimuli. As an example, the stimuli may be provided in a form, in which at least one or two or more of "temperature stimulus (a heating stimulus/a cooling stimulus)", "a pressure stimulus (a pressure sense)", "an electric stimulus (for example, deterioration of biological tissues by a radio frequency (RF) current)", "a haptic stimulus (for example, vibration)", "a fluidic stimulus (for example, ejection of gas)", and "a brush stimulus (a comfortable stimulus that brushes against skin with fine ultrafine yarns)" are combined, but the present disclosure is not limited thereto. For example, for a chronic pain patient, the temperature stimuli may be used as stimuli for perception training by using the features, in which the temperature stimuli and the pain stimuli are perceived through the same nerve route anatomically. That is, the stimulus providing units 12 may provide temperature stimuli to allow the user to perform a perception training for pain generated while body tissues are not damaged (that is, generated without an injury).

A detailed description of the scheme of providing various types of stimuli by the stimulus providing units will be made later.

Furthermore, as another embodiment, the stimulus providing device 10 may control a stimulus providing time such that a stimulus may not be adapted. For example, after providing stimuli for a first period of time to the same location, the stimulus providing device 10 may provide a pause for a second period of time. Through this, the stimulus providing device 10 may perform a treatment such that one body portion is not adapted to the stimuli while providing stimuli for the pain treatment to the body portion. In detail, after providing stimuli for the first period of time, the stimulus providing device 10 may repeat a process of arranging a time interval, in which a stimulus is not provided for the second period of time.

Figure 2:
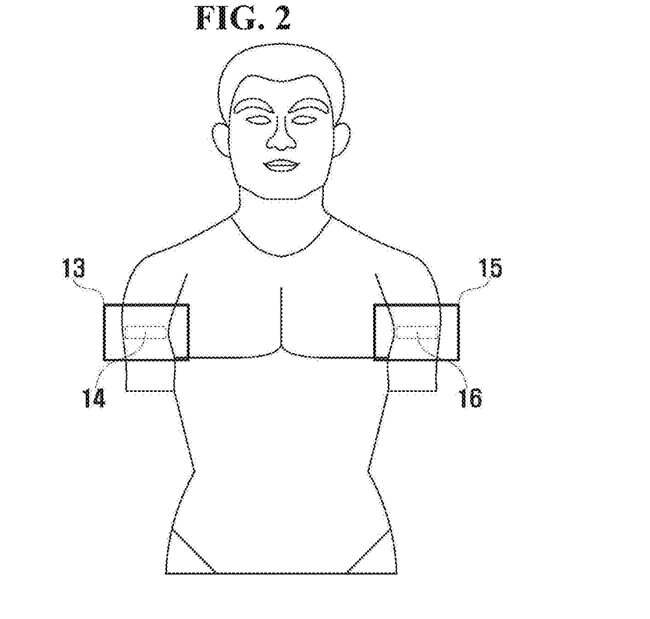
Figure 3A:
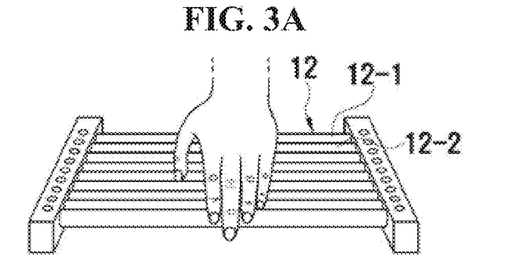
FIGS. 3A to 3C are conceptual views illustrating various embodiments of a stimulus providing unit of a stimulus providing device of the inventive concept.
Figure 3B:
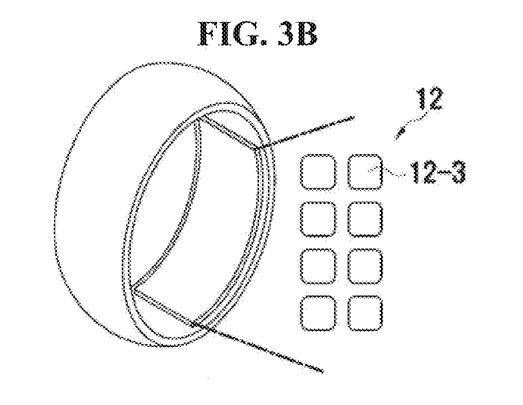
Figure 3C:
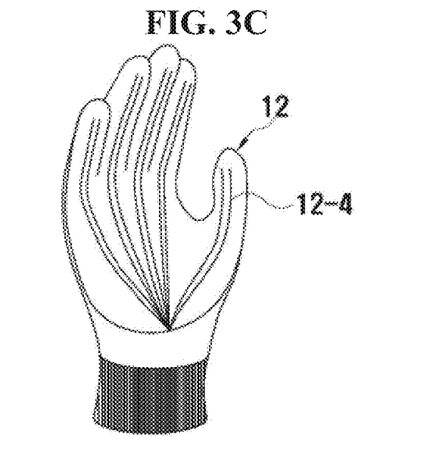

Moreover, referring to FIG. 2, the mounting units 11 may include a first mounting unit 13 and a second mounting unit 15 that are mounted on different body portions, among the plurality of body portions of the user. That is, the first mounting unit may be mounted on a first body portion of the user (that is, a patient) and the second mounting unit may be mounted on a second body portion of the user such that stimuli may be provided to several body portions. As an embodiment, the first mounting unit 13 may be mounted on a normal body portion, and the second mounting unit 15 may be mounted on an abnormal body portion. Through this, a training for distinguishing the stimuli provided to the first body portion and the second body portion of the patient may be performed.

Further, as another embodiment, when passive stimuli are provided to the patient while the stimuli are not distinguished, the stimulus providing location may be changed to the first body portion and the second body portion such that the patient is not adapted to the stimuli provided by the stimulus providing units. For example, when the patient mainly feels pain at several locations, the first body portion and the second body portion become the pain portions, to which the pain stimuli are to be provided.

To achieve this, when the mounting units 11 includes the first mounting unit 13 and the second mounting unit 15, the stimulus providing units 12 may include a first stimulus providing unit 14 that provides stimuli to a body portion (for example, a normal body portion), on which the first mounting unit 13 is mounted, and a second stimulus providing unit 16 that provides stimuli to a body portion (for example, an abnormal body portion), on which the second mounting unit 15 is mounted.

The stimulus providing units 12 may provide stimuli in various schemes. As an example, the stimulus providing units 12, as illustrated in FIG. 3A, may include one or more first strips 12-1 that provides a first temperature and one or more second strips 12-2 that provides a second temperature.

In this case, the one or more first strips 12-1 and the one or more second strips 12-2 may be arranged in a stripe pattern form, in which they are alternately arranged.

Furthermore, the first temperature may be higher than a surface temperature of a body portion (a heating stimulus), and the second temperature may be lower than the surface temperature or the body portion (a cooling stimulus).

As a result, the stimulus providing units 12 may provide cooling stimuli and heating stimuli that are alternately repeated, and may allow the user to perceive "virtual stimuli". Meanwhile, the "virtual stimuli" are stimuli generated due to a phenomenon called a thermal grill illusion, and for example, may be painful stimuli that are felt as the brain of the user creates an illusion when metal strips set to 40° C. and 20° C. are disposed alternately and contact the body portions.

Furthermore, the stimulus providing units 12, as illustrated in FIG. 3B, may include a plurality of segments 12-3 driven to provide stimuli. In this case, the plurality of segments 12-3 may be arranged along one or more rows and one or more columns.

Furthermore, the plurality of segments 12-3 may be driven in various schemes. As an example, the plurality of segments 120-3 may selectively protrude to provide pressure stimuli, and may selectively receive electric energy to provide electric stimuli, but the inventive concept is not limited thereto.

Furthermore, the stimulus providing units 12, as illustrated in FIG. 3C, may include a plurality of heat emitters 12-4. In this case, the plurality of heat emitters 12-4 may be provided in a form of heating wires.

Further, the stimulus providing units 12 may provide pressure stimuli (pressure senses). For example, the stimulus providing units may include protrusion modules, the protrusion levels of which are controlled, and the intensities of the pressure stimuli provided to the patient may be adjusted by controlling the protrusion levels. Furthermore, when the stimulus providing units include a plurality of protrusion modules, the intensities of the pressures may be adjusted by adjusting the number of protrusions. The tips of the protrusion modules, which press the skin of the patient, may be obtuse or sharp.

Furthermore, the stimulus providing units 12 may be provided with one or more electrodes that provide a radio frequency (RF) current, on a 2-dimensional plane. Then, the stimulus providing units output RF currents to electrodes with an RF module. In detail, the stimulus providing units may be manufactured in a bipolar scheme, in which a plurality of electrodes have a (+) electrode and a (−) electrode, such that the patient may not wear a separate configuration, in addition to the stimulus providing device. Through this, the patient may feel electric stimuli, and the skin of the patient is heated by an RF current of a specific intensity or more so that the patient may feel temperature stimuli together.

Furthermore, the stimulus providing units 12 may include one or more haptic modules, and may generate haptic stimuli with a control unit, which will be described below. The haptic modules adjust the intensities of the haptic stimuli output by the control unit, which will be described below.

Furthermore, as another embodiment, the stimulus providing device may be controlled by the control unit in a physically separated device (for example, a smartphone of the patient that interworks with the stimulus providing device) or may be controlled by the control unit in the stimulus providing device. For example, when the stimulus providing device interworks with the user terminal to be used, the user terminal and one or more stimulus providing devices may constitute a stimulus providing training system.

The control unit (not illustrated) functions to set stimuli that are to be provided through the stimulus providing unit. As an example, the control unit may control at least one of the location, the range, and the intensity of the stimuli. Accordingly, the stimulus providing device 10 of the inventive concept may provide stimuli in various methods. As a result, the user may receive stimuli in various schemes according to the condition of the user to perform a perception training.

Meanwhile, the locations of the stimuli may mean the location, to which the stimuli are provided, and the point of one body portion, to which the stimuli are provided, may be changed by changing the location of the stimuli and the body portion itself may be changed. For example, when stimuli are provided to several body portions (for example, the patient wears the first mounting part provided with the first stimulus providing unit and the second mounting unit provided with the second stimulus providing unit), the control unit may set locations (for example, a location at which the first stimulus providing unit is disposed and a location at which the second stimulus providing unit is disposed), to which stimuli are to be provided.

Furthermore, the range of the stimuli may mean the range, in which the stimuli are provided at a specific location, and when the stimulus providing units 12 include the plurality of segments 12-3, the plurality of segments 12-3 may be controlled by selectively driving the plurality of segments 12-3.

Furthermore, the intensity of the stimuli may mean an absolute value or a relative value of the stimuli provided to a specific location in a specific range. Meanwhile, for a perception disorder patient, the intensity of the stimuli provided actually and the intensity of the stimuli perceived by the patient may be different, and accordingly, the patient may appeal various disorders (for example, chronic pain).

Meanwhile, the stimuli may be a plurality of stimuli, and in this case, at least one of the locations and the intensity of at least some of the plurality of stimuli may be different.

Furthermore, as an embodiment, the control unit may control the stimulus providing units 12 in "a passive mode" and "a training mode".

In the "passive mode", stimuli are provided to a body portion by a predetermined number of times, but the user may not be required to distinguish the stimulus provided to the user to select an answer. That is, because stimuli are continuously provided to a specific body portion in the "passive mode", a negative symptom of an abnormal body portion, a positive symptom of an abnormal brain due to deterioration of sensing functions, or the like may be normalized. In this case, the location, the range, and the intensity of the stimuli may be constantly maintained or changed for a predetermined number of times, but it may be preferable that they are constantly maintained.

Hereinafter, a detailed description of a mode (hereinafter, referred to as "a manual stimulus mode" or "a passive mode"), in which the patient manually receives stimuli without a process of distinguishing a stimulus by the patient, will be made.

As an embodiment, the manual stimulus mode may be implemented in a scheme of providing stimuli to a body portion, of which pain the patient feels, or a body portion having the same nerve route as the body portion, of which pain the patient mainly feels.

Furthermore, as another embodiment, the manual stimulus mode may provide a stimulus at the location, at which the stimulus providing unit is disposed, at a timing that is suitable for providing a manual stimulus for alleviation of pain. For example, because the patients often do not feel pain while moving, manual stimuli may be provided during rests, during which the patients do not move. In detail, because phantom pain caused when the brain of the patient determines that there is a stimulus even though there is no actual stimulus generally corresponds to a situation, in which a sensory stimulus (sensory input) actually is not introduced to the brain, a stimulus is provided at a timing (for example, during a rest), at which a sensory stimulus is not input.

Furthermore, as another embodiment, the control unit functions to judge or determine a timing that is suitable for providing a manual stimulus to the patient. For example, the control unit may calculate a timing, at which it is determined that there is no sensory stimulus (that is, a stimulus applied to skin at a portion at which pain is mainly felt) in the patient, and may request the stimulus providing unit to output a set stimulus. For example, when the stimulus providing device includes a motion sensor such as a gyro sensor, the control unit may sense a state in which the patient does not move, and then request the stimulus providing unit to output a stimulus. That is, the control unit may determine a timing that is suitable for passive perceptual learning, and may improve a perception training effect for treatment of pain.

Furthermore, as another embodiment, the control unit may change a stimulus form or a stimulus level according to a situation of the patient. In a situation in which the patient takes a rest and a situation in which the patient moves, degrees of perceiving stimuli may be different. That is, the control unit may determine whether the patient is moving, and may make the intensities of the provided stimuli different (for example, the intensities of the stimuli are increased when the patient moves).

Furthermore, as another embodiment, the control unit sets the stimuli of the intensities, by which the patient does not feel pain, so that the patient does not feel during the training. Because the references of the intensities of the stimuli perceived as pain may be different according to the patients, the control unit sets the intensities of the stimuli of an appropriate level to the patient who performs a manual stimulus based perception training to provide the training.

To achieve this, as an embodiment, the control unit may receive feedbacks from the patient while adjusting the intensities of the stimuli provided to the patient, and may set an appropriate intensity of the stimuli. As another embodiment, the control unit may be connected to a separate brainwave measuring device to set a stimulus that has a high brain activation level while the patient does not feel pain. The appropriate intensity of the stimulus may be set through a brainwave measuring device of the patient, and the appropriate intensity of the stimulus may be set based on brainwaves and feedbacks to the pain level of the patient that are acquired while the intensities of the stimuli are adjusted in a hospital.

Unlike this, in "a training mode or an active mode (a training mode in which the patient distinguishes stimuli provided simultaneously or sequentially)", the stimuli are provided to the body portions a predetermined number of times, and thus the patient may be requested to select an answer by distinguishing the stimuli provided to the user. That is, in "the training mode", because stimuli are proved to an abnormal body portion while being changed and the user perceives the changes of the stimuli, deterioration of sensory functions for the abnormal body portion, activation of the abnormal brain due to the deterioration of sensory functions, or the like may be normalized. In this case, the location, the range, and the intensity of the stimuli may be constantly maintained or changed for a predetermined number of times, but it may be preferable that they are changed.

When a perception disorder patient is a chronic pain patient, he or she feels pain because his or her brain generates a stimulus signal in an abnormal route as the stimulus sensitivity decreases (for example, the threshold value for the stimulus becomes higher), and accordingly, chronic pain may be solved by improving the brain such that the stimulus is delivered through a proper nervous delivery route through a training in a "passive mode" and a "training mode".

Various training methods in the "training mode" will be described in detail in a description of a perception training method of the inventive concept.

Furthermore, as another embodiment, the control unit may set at least one of the location, the range, and the intensity of stimuli according to the number of receptors of the body portion, to which the stimuli are provided. As described above, the body portion, to which the stimuli are provided, may be primarily determined by the mounting units 11, and may be secondarily determined as the control units determine the location of the stimuli.

Furthermore, as another embodiment, the control unit may control the stimulus providing units 12 in a "heat retaining mode" and a "stimulus providing mode", and as an example, when the mounting units 11 are provided in a form of grooves and the stimulus providing units 12 include a plurality of heat emitters 12-4, the stimulus providing units 12 may provide a temperature for retaining heat of the body portion in the "heat retaining mode" and may provide a temperature for stimulating the body portion in the "stimulus providing mode".

Hereinafter, the perception training method of the inventive concept will be described with reference to the drawings. FIGS. 4 to 9 are flowcharts illustrating various embodiments of a perception training method of the inventive concept.

Figure 4:
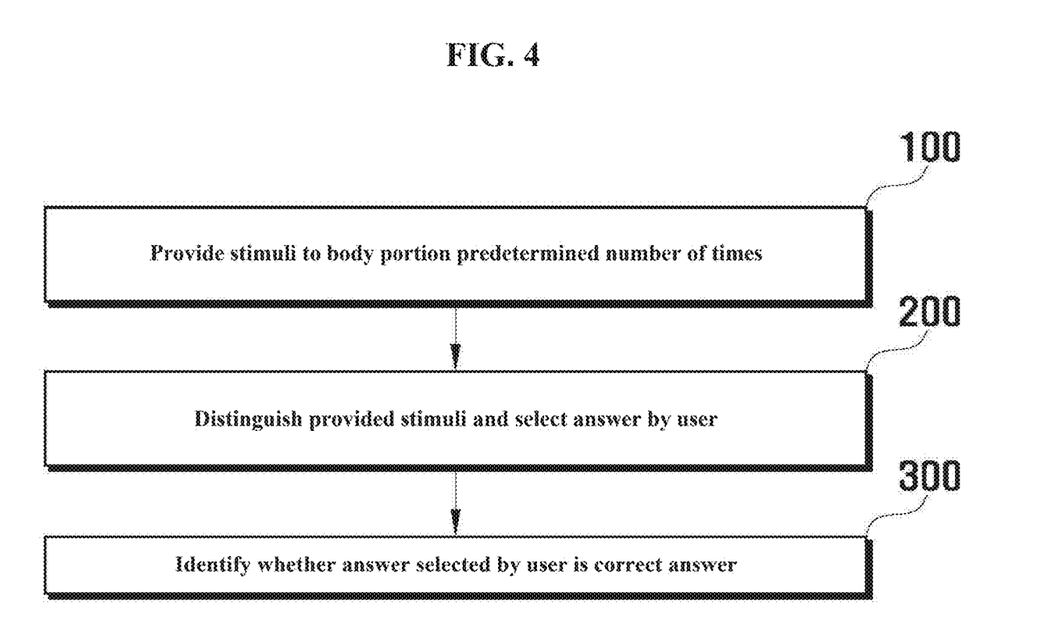
FIGS. 4 to 9 are flowcharts illustrating various embodiments of a perception training method of the inventive concept.

Hereinafter, a perception training method of a first embodiment of the inventive concept will be described with reference to FIG. 4. The perception training method of the first embodiment of the inventive concept may include a stimulus providing operation 100, a request operation 200, and a correct answer identifying operation 300.

In the stimulus providing operation 100, the control unit may provide stimuli to a body portion a predetermined number of times. In the request operation 200, the control unit may request the user to distinguish the stimuli provided to the user and select an answer. In the correct answer identifying operation 300, the control unit may identify whether the answer selected by the user is a correct answer.

That is, in the perception training method of the first embodiment of the inventive concept, stimuli may be provided to the user a predetermined number of times, and it may be identified whether the user distinguishes the stimuli according to the selection by the user.

As described above, the perception disorder patient appeals various symptoms because the actual stimuli and the stimuli perceived by the patient do not coincide with each other. In the perception training method of the first embodiment of the inventive concept, a sensory function may be normalized by checking whether the perception disorder patient recognized the stimuli rightly by himself and herself.

Meanwhile, in the perception training method of the first embodiment of the inventive concept, the stimuli may be virtual stimuli generated by providing a first temperature that is higher than a surface temperature of the body portion and a second temperature that is lower than the surface temperature of the body portion.

In this case, in the stimulus providing operation 100, a difference between the first temperature and the second temperature may be changed for the number of times, and in the request operation 200, the control unit may request the user to distinguish a change of the difference between the first temperature and the second temperature for the number of times to select the intensity (the intensity of pain) of the virtual stimuli perceived by the user.

That is, in the perception training method of the first embodiment of the inventive concept, unlike the conventional perception training, the user may check whether the intensity of virtual stimuli are perceived rightly to perform a perception training by using the fact that the intensity of the virtual stimuli (the intensity of pain generated as the brain causes an illusion) is changed according to the difference between the first temperature and the second temperature that generate the virtual stimuli.

Furthermore, a training method of a modification of the first embodiment of the inventive concept provides a perception training method of another scheme using virtual stimuli.

In this case, in the stimulus providing operation 100, a difference between the first temperature and the second temperature may be constant for the number of times, and the values of the first temperature and the second temperature may be changed, and in the request operation 200, the control unit may request the user to distinguish a change of the values of the first temperature and the second temperature for the number of times to select the intensity of the virtual stimuli perceived by the user.

That is, in another perception training method of the first embodiment of the inventive concept, the intensity of virtual stimuli may be adjusted by changing the values of the first temperature and the second temperature (changing a base line) by the control unit even though the difference between the first temperature and the second temperature is constant, and a perception training may be performed by checking whether the user perceived the intensity of the virtual stimuli rightly according to the change in the base line.

Further, in a perception training method of another modification of the first embodiment of the inventive concept, in the stimulus providing operation 100, the control unit may change at least one of the location, the range, and the intensity of the stimuli for a predetermined number of times. Moreover, in the request operation 200, the control unit may request the user to distinguish at least one of the location, the range, and the intensity of the stimuli for the number of times and to select at least one of the location, the range, and the intensity of the stimuli perceived by the user.

Further, in a perception training method of another modification of the first embodiment of the inventive concept, in the stimulus providing operation 100, a plurality of stimuli are provided for the predetermined number of times and at least one of the location, the range, and the intensity of at least some of the plurality of stimuli may be different. That is, in one process, a plurality of stimuli, of which at least one of the location, the range, and the intensity of some are different, may be provided. Moreover, in the request operation 200, the control unit may request the user to distinguish at least one of the location, the range, and the intensity of at least some of the plurality of stimuli for the number of times and to select a stimulus, among the plurality of stimuli perceived by the user, which satisfies a specific condition.

As an example, when the stimulus providing device 10 for performing another modification of the first embodiment of the inventive concept is provided in a glove form, a plurality of stimuli may be provided to an index finger, a middle finger, and a ring finger, and the user may be requested to select a stimulus, among the plurality of stimuli, which has the largest intensity.

Figure 5:
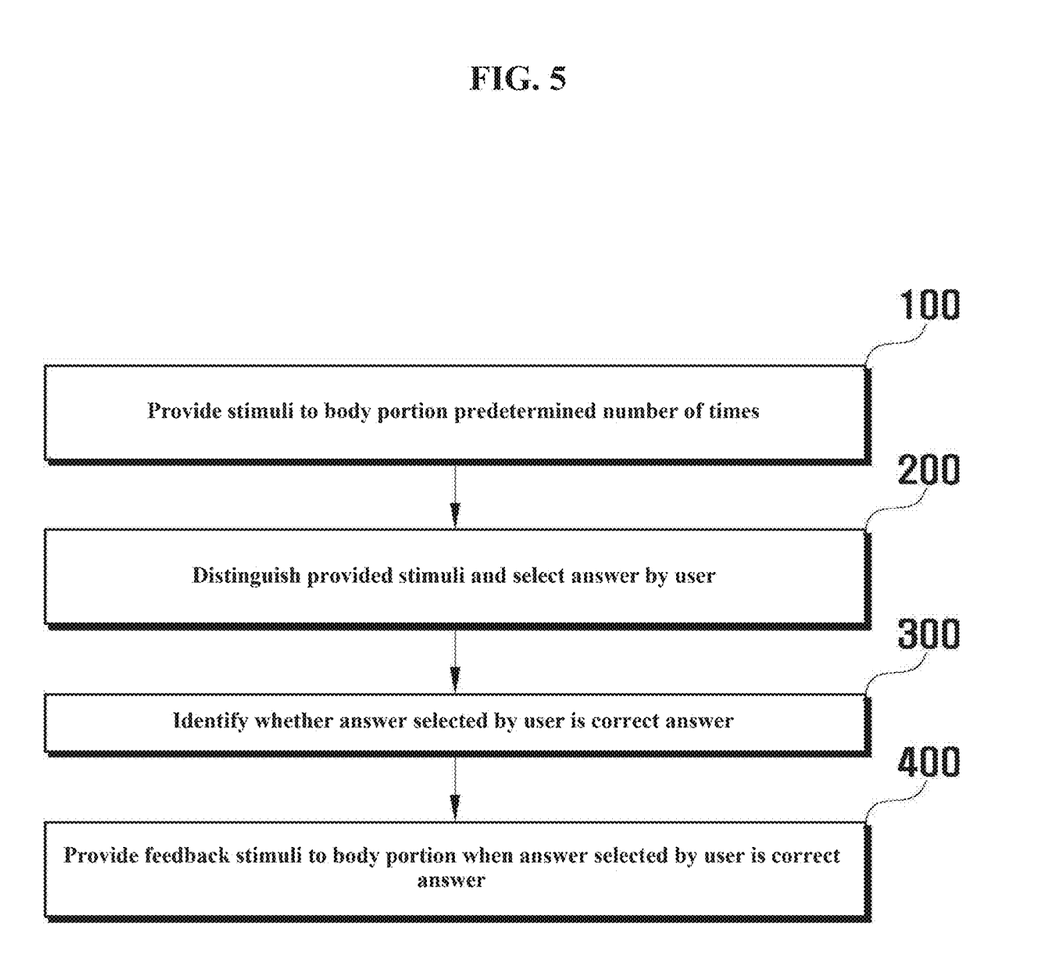

Hereinafter, a perception training method of a second embodiment of the inventive concept will be described with reference to FIG. 5. Like the perception training method of the first embodiment of the inventive concept, the perception training method of the second embodiment of the inventive concept may include the stimulus providing operation 100, the request operation 200, and the correct answer identifying operation 300. Moreover, the perception training method of the second embodiment of the inventive concept may further include a feedback operation 400.

In the feedback operation 400, when the answer selected by the user is a correct answer, the control unit may provide a feedback stimulus according to the correct answer to the user. In this case, the feedback stimulus may be provided after a predetermined number of times, or may be provided for each of times. Furthermore, the feedback stimulus may be provided to the same body portion as the stimuli provided in the stimulus providing operation 100. Further, the feedback stimuli may be comfortable stimuli, and for example, may be brush stimuli.

Figure 6:
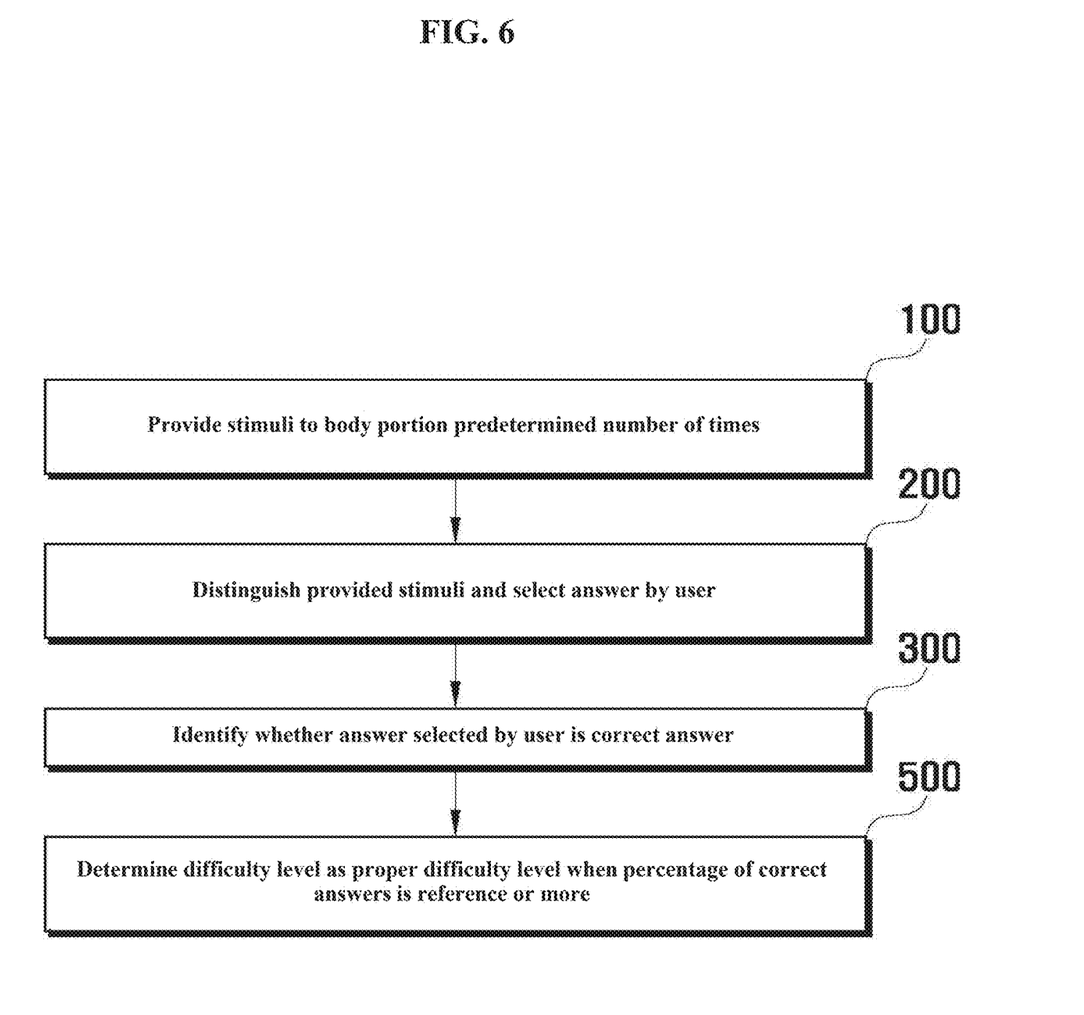

Hereinafter, a perception training method of a third embodiment of the inventive concept will be described with reference to FIG. 6. Like the perception training method of the first embodiment of the inventive concept, the perception training method of the third embodiment of the inventive concept may include the stimulus providing operation 100, the request operation 200, and the correct answer identifying operation 300. Moreover, the perception training method of the third embodiment of the inventive concept may further include a difficulty level determining operation 500.

In the difficulty level determining operation 500, when the percentage of correct answers in the correct answer identifying operation 300 is a reference or more, the control unit may determine that the difficulty level is a proper one. Moreover, when it is determined that the difficulty level is a proper one, the training may be performed again while the stimulus condition in the stimulus providing operation 100 may be maintained.

Meanwhile, the user may distinguish the virtual stimuli better such that the location, the range, and the intensity of the stimuli are changed more greatly as the intensity of the virtual stimuli becomes larger, and accordingly, the percentage of correct answers increases In the perception training method of the third embodiment of the inventive concept, the control unit may allow the user to repeatedly perform an optimum perception training by setting a proper difficulty level when the stimuli is a specific change rate or more.

Figure 7:
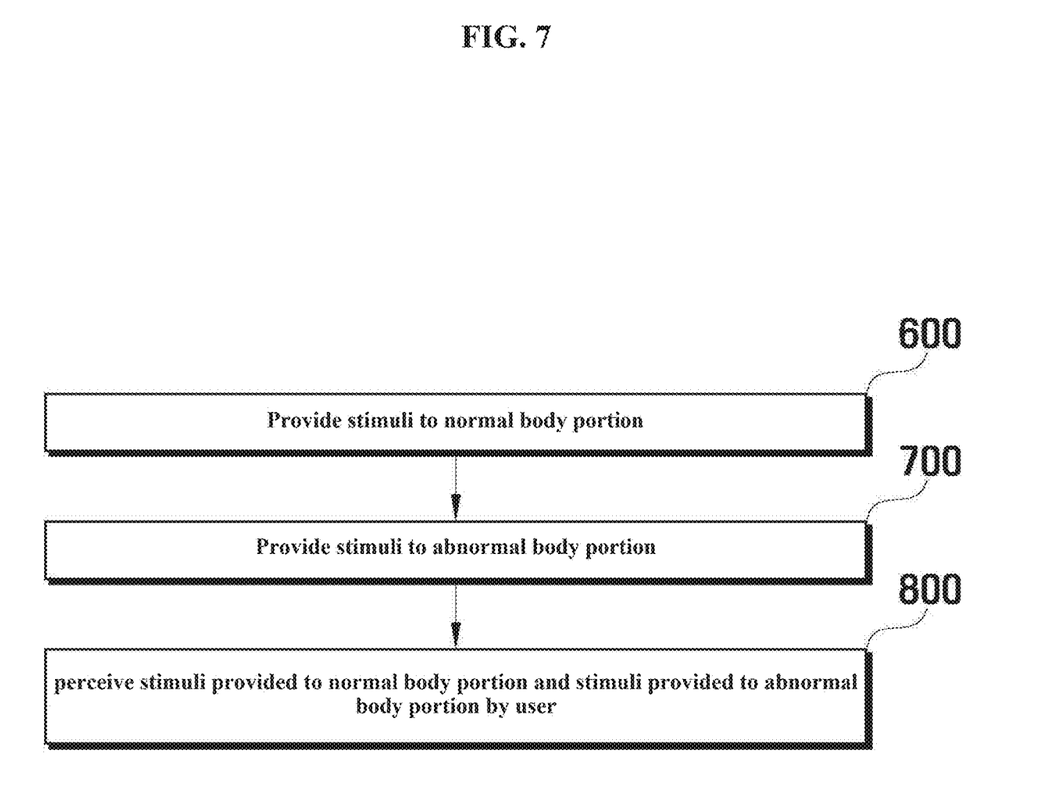

Hereinafter, a perception training method of a fourth embodiment of the inventive concept will be described with reference to FIG. 7. The perception training method of the fourth embodiment of the inventive concept may include a normal body portion stimulus providing operation 600, an abnormal body portion stimulus providing operation 700, and a perception operation 800.

In the normal body portion stimulus providing operation 600, the control unit may provide stimuli to a normal body portion, in the abnormal body portion stimulus providing operation 700, the control unit may provide stimuli to an abnormal body portion, and in the perception operation 800, the user may perceive the stimuli provided to the normal body portion and the stimuli provided to the abnormal body portion.

That is, because the chronic pain is caused at a specific body portion, when the same stimuli as those of the normal body portion are provided, the patient may learn that the provided stimuli is not strong enough to be felt as pain.

Because the user recognizes the stimuli provided to the normal body portion rightly, he or she may effectively normalize the sensory function by recognizing that the stimuli provided to the abnormal body portion and the stimuli actually felt by himself or herself are different.

Moreover, in order to maximize the above-described effects, the normal body portion and the abnormal body portion may be symmetrical to each other. As an example, when the normal body portion is the wrist of a left arm, the abnormal body portion may be the wrist of a right arm, but the inventive concept is not limited thereto.

Meanwhile, according to the condition of the patient, the normal body portion stimulus providing operation 600 and the abnormal body portion stimulus providing operation 700 may be performed simultaneously or at different times.

Meanwhile, in the stimulus providing device 10 that performs the perception training method of the fourth embodiment of the inventive concept, when the mounting units 11 include the first mounting unit 13 and the second mounting unit 15 and the stimulus providing units 12 include the first stimulus providing unit 14 and the second stimulus providing unit 16, the first mounting unit 13 may be disposed at the normal body portion and stimuli may be provided by the first stimulus providing unit 14 and the second mounting unit 15 may be disposed at the abnormal body portion and stimuli may be provided by the second stimulus providing unit 16.

Until now, although the perception training method of the fourth embodiment of the inventive concept has been described with reference to the "passive mode" that simply provides stimuli to a body portion, the perception training method of the fourth embodiment of the inventive concept is not limited thereto.

That is, the perception training method of the fourth embodiment of the inventive concept may be also realized in the "training mode", as in the perception training method of the first embodiment of the inventive concept, stimuli may be provided to a normal body portion and an abnormal body portion a predetermined number of times, the user may be requested to distinguish the stimuli provided to the user and to select an answer, and it may be identified whether the answer selected by the user is a correct answer.

Figure 8:
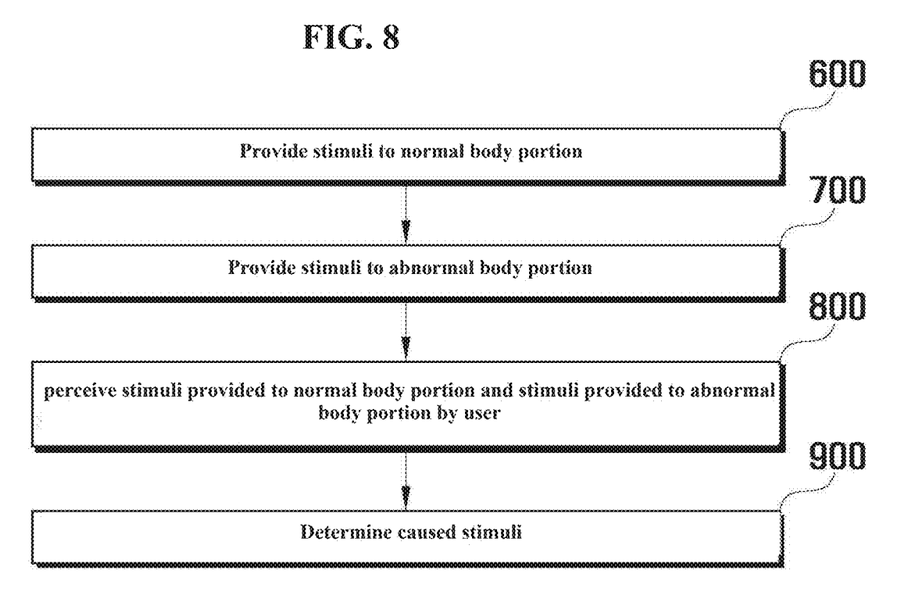

Hereinafter, a perception training method of a fifth embodiment of the inventive concept will be described with reference to FIG. 8. Like the perception training method of the fourth embodiment of the inventive concept, the perception training method of the fifth embodiment of the inventive concept may include the normal body portion stimulus providing operation 600, the abnormal body portion stimulus providing operation 700, and the perception operation 800. Moreover, the perception training method of the fifth embodiment of the inventive concept may further include a caused stimulus determining operation 900.

A perception disorder patient may appeal pain of an abnormal body portion not by stimuli provided to an abnormal body portion but by stimuli (caused stimuli) provided to a normal body portion according to the type of the patient.

In this case, as long as a normal body portion (hereinafter, a caused stimulus body portion), to which caused stimuli are provided, may be determined, a solution on demand may be provided to the perception disorder patient.

To achieve this, in the caused pain determining operation 900, when the user perceives stimuli of a specific intensity or more at an abnormal body portion in the normal body portion stimulus providing operation 600 and the user does not perceive stimuli of the specific intensity or more at the abnormal body portion in the abnormal body portion stimulus providing operation 700, the control unit may determine that the normal body portion is a stimulus causing body portion.

Figure 9:
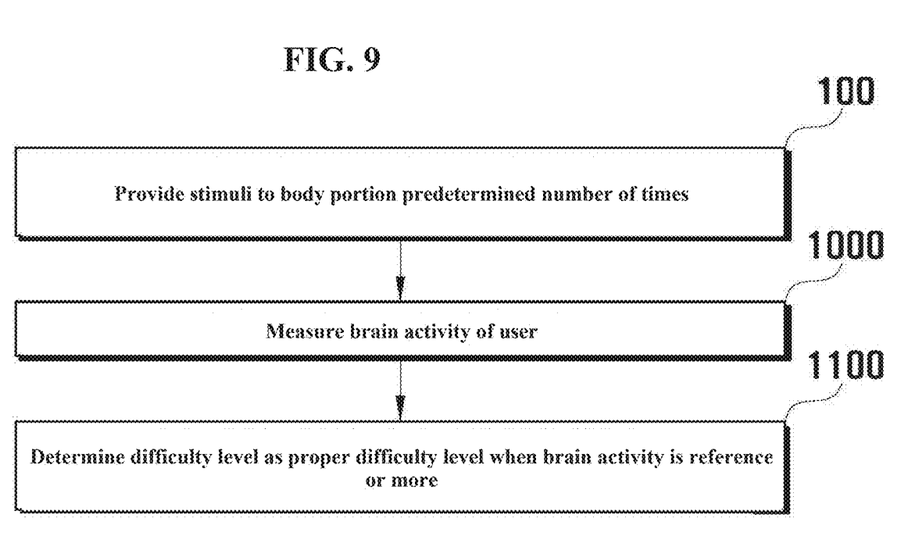

Hereinafter, a perception training method of a sixth embodiment of the inventive concept will be described with reference to FIG. 9. The perception training method of the sixth embodiment of the inventive concept may include the stimulus providing operation 100, an operation 1000 of measuring a brain activity of the user, and a difficulty level determining operation 1100. That is, in the perception training method of the sixth embodiment of the inventive concept, it may be determined that stimuli are provided at a proper difficulty level when the brain activity of the user according to the stimuli is measured and the brain activity is a reference or more (the brain activity is high in the stimulus providing operation).

Further, a perception training method of another embodiment of the inventive concept may include sequentially providing a plurality of stimuli generated by the stimulus providing device mounted on body portions of a user to a specific body portion of the user or simultaneously providing the plurality of stimuli to a plurality of body portions of the user, wherein at least one of a location, a range, and an intensity of the plurality of stimuli is different, distinguishing a stimulus provided to the user, requesting the user to select an answer corresponding to the distinguished stimulus, and determining whether the selected answer of the user is a correct answer.

The method according to the embodiment of the inventive concept described above may be coupled to the computer that is a hardware element to be implemented in a program (or an application) to be executed and may be stored in a medium.

A 'computer' includes all various devices that may provide a user with a result by performing a calculation. For example, the computer may correspond to a smartphone, a tablet PC, a cellular phone, a personal communication service (PCS) phone, a mobile terminal of a synchronous/asynchronous international mobile telecommunication (IMT)-2000, a palm personal computer (PC), and a personal digital assistant (PDA), in addition to a desktop computer and a notebook. Further, the computer may be a server that receives a request from the client and process information.

The program may include a code that is coded in a computer language, such as C, C++, JAVA, or a machine language, by which a processor of the computer may be read through a device interface of the computer, to execute the methods implemented by a program after the computer reads the program. The code may include a functional code related to a function that defines necessary functions that execute the methods, and the functions may include an execution procedure related control code necessary to execute the functions in its procedures by the processor of the computer. Further, the code may further include additional information that is necessary to execute the functions by the processor of the computer or a memory reference related code on at which location (address) of an internal or external memory of the computer should be referenced by the media. Further, when the processor of the computer is required to perform communication with another computer or server in a remote site to allow the processor of the computer to execute the functions, the code may further include a communication related code on how the processor of the computer executes communication with another computer or server or which information or medium should be transmitted and received during communication by using a communication module of the computer.

The stored medium refers not to a medium, such as a register, a cash, or a memory, which stores data for a short time but to a medium that stores data semi-permanently and is read by a device. In detail, an example of the stored medium may include a ROM, a RAM, a CD-ROM, a magnetic tape, a floppy disk, and an optical data storage device, but the present invention is not limited thereto. That is, the program may be stored in various recording media on various servers, which the computer may access, or in various recording media on the computer of the user. Further, the media may be dispersed in a computer system connected to the medium through a network, and codes that may be read by the computer in a dispersion manner may be stored.

The inventive concept provides a stimulus providing device that may normally activate the brain of a patient in various stimulation methods. Moreover, the inventive concept provides a perception training method using the stimulus providing device, and a computer program stored in a medium to perform the perception training method.

The effects of the inventive concept are not limited thereto, and other unmentioned effects of the inventive concept may be clearly appreciated by those skilled in the art from the following descriptions.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A stimulus providing device for providing a training stimulus for improving pain, the stimulus providing device comprising:
   one or more mounting units configured to be mounted on body portions of a user; and
   one or more stimulus providing units disposed on the mounting units and configured to provide stimuli to the body portions,
   wherein the stimulus providing units are controlled by a control unit included in the stimulus providing device or a control unit physically separated from the stimulus providing device to interwork with the stimulus providing device and included in a terminal of the user,
   wherein the control unit controls at least one of a location, a range, and an intensity of the stimuli,
   wherein the stimulus providing units include:
   a plurality of first strips that configured to provide a first temperature that is higher than a temperature of a body surface of the user, to the body portions of the user; and
   a plurality of second strips configured to provide a second temperature that is lower than the temperature of the body surface of the user, to the body portions of the user, and
   wherein the plurality of first strips and the plurality of second strips are arranged in a form of a stripe pattern, in which each first strip of the plurality of first strips and each second strip of the plurality of second strips are alternately arranged.

2. The stimulus providing device of claim 1, wherein the control unit is configured to:
   detect a timing, at which a sensory stimulus is not input to the user, and
   manually output stimuli through the stimulus providing units at the detected timing.

3. The stimulus providing device of claim 2, wherein the control unit is configured to, while adjusting the intensities of the stimuli by stages, receive whether pain is felt due to the intensities of the stimuli adjusted by stages and determine appropriate intensities of stimuli.

4. The stimulus providing device of claim 2, wherein the control unit is configured to determine appropriate intensities of stimuli, which cause the user to maintain brain activation levels at or above a reference value without feeling pain.

5. The stimulus providing device of claim 1, wherein the control unit is configured to:
   control the one or more stimulus providing units to sequentially provide the stimuli to a specific body portion of the user or simultaneously provide the stimuli to a plurality of body portions of the user;
   distinguish a stimulus provided to the user;
   request the user to select an answer corresponding to the distinguished stimuli; and
   determine the selected answer is a correct answer.

6. The stimulus providing device of claim 5, wherein the correct answer is a stimulus that coincides with a specific condition or different stimuli among three or more stimuli.

7. The stimulus providing device of claim 1, wherein the stimulus providing units include a plurality of heat emitters, and
   wherein the control unit controls the stimulus providing units in a heat retaining mode and a stimulus providing mode.

8. The stimulus providing device of claim 1, wherein the mounting units include:
   a first mounting unit configured to be mounted on a first body portion of the user; and
   a second mounting unit configured to be mounted on a second body portion of the user, and
   wherein the stimulus providing units include:
   a first stimulus providing unit disposed in the first mounting unit and configured to provide a stimulus to the first body portion; and
   a second stimulus providing unit disposed in the second mounting unit and configured to provide a stimulus to the second body portion.

\* \* \* \* \*